US00PP15199P2

(12) United States Plant Patent
van Dijk

(10) Patent No.: US PP15,199 P2
(45) Date of Patent: Oct. 5, 2004

(54) ***ANTHURIUM ANDREANUM* PLANT NAMED 'ANTHBNENA'**

(50) Latin Name: *Anthurium andreanum L*
Varietal Denomination: Anthbnena

(75) Inventor: Jan van Dijk, Bleiswijk (NL)

(73) Assignee: Anthura B.V. (NL)

( * ) Notice: Subject to any disclaimer, the term of this patent is extended or adjusted under 35 U.S.C. 154(b) by 0 days.

(21) Appl. No.: 10/452,915

(22) Filed: Jun. 3, 2003

(51) Int. Cl.[7] ..... A01H 5/00

(52) U.S. Cl. ..... Plt./365

(58) Field of Search ..... Plt./365

(56) References Cited

PUBLICATIONS

UPOV hit on 'Anthbnena', UPOV–ROM, Plant Variety Database, 2003/03.*

* cited by examiner

*Primary Examiner*—Anne Marie Grunberg
(74) *Attorney, Agent, or Firm*—Foley & Lardner LLP

(57) ABSTRACT

A new and distinct cultivar of *Anthurium andreanum* plant named 'Anthbnena', as described and illustrated, and particular characterized by the combined features of compact plant growth and early and rich flowering; flowering freely throughout the year; mini-type pot plant; maximum growth to approximately 40 cm; long and erect peduncle, flowers held well above the foliage; full plant habit due to rich shoot formation; dark green leaves, very compact and durable; red flowers, reasonably durable remaining red until they die; large amount of flowers in relation to the amount of leaves resulting in excellent leaf to flower size ratio.

4 Drawing Sheets

Latin name of the genus and species of the plant claimed: *Anthurium andreanum* L.
Variety denomination: Anthbnena.

BACKGROUND OF THE INVENTION

'Anthbnena' is a new and distinct cultivar of *Anthurium,* botanically known as *Anthurium andreanum* L. The new cultivar is a product of a planned breeding program, and was obtained from a cross made during such a program in Bleiswijk, The Netherlands, in 1996.

The female or seed parent was a pink-colored *Anthurium* pot plant identified as number 95-634-01 (unpatented). The male or pollen parent was an orange-colored flowering *Anthurium* pot plant identified as number 95-532-02 (proprietary, unpatented). 'Anthbnena' was discovered and selected as a flowering plant within the progeny of the stated cross by the inventor, Jan van Dijk, in March, 1998 in a controlled environment in a glasshouse in Bleiswijk, The Netherlands.

Subsequent asexual reproduction by tissue culture at the same location has demonstrated that the combination of characteristics as herein disclosed for the new cultivar are firmly fixed and are retained through successive generations of asexual reproduction.

BRIEF DESCRIPTION OF THE INVENTION

The following traits have been repeatedly observed and in combination distinguish 'Anthbnena' as a new and distinct cultivar:

1. Compact plant growth and early and rich flowering;
2. Flowering freely throughout the year;
3. Mini-type pot plant; maximum growth to approximately 40 cm;
4. Long and erect peduncle, flowers held well above the foliage;

5. Full plant habit due to rich shoot formation;
6. Dark green leaves, very compact and durable;
7. Red flowers, reasonably durable remaining red until they die;
8. Large amount of flowers in relation to the amount of leaves resulting in excellent leaf to flower size ratio.

BRIEF DESCRIPTION OF THE DRAWINGS

The accompanying photographs, taken in Bleiswijk, The Netherlands, show typical 'Anthbnena' specimens.

FIG. 1 is a side-view of 'Anthbnena' showing the flowers held well above the leaf canopy.

FIG. 2 is a close-up of a 'Anthbnena' flower showing the spathe and spadix.

FIG. 3 is a close-up of 'Anthbnena' flowers at three different development stages: from young on the left to old on the right. The youngest flower has an unripe spadix (pistils and pollen are not visible yet). The flower in the middle has a ripe spadix. The spathe of the old flower on the right becomes brown-red and the spadix becomes green. The lobes of the flower could curve backwards with age. Between the left and the right flowers is a difference in age of approximately 8 to 10 weeks.

FIG. 4 is a close-up of the top of a young (left) and old leaf blade (right) showing the difference between the colour of a young and old leaf blade. It also shows that the young leaf blades are more shiny then the old leaf blades.

DETAILED BOTANICAL DESCRIPTION

The following observations, measurements and values describe plants grown in Bleiswijk, The Netherlands, under greenhouse conditions, which closely approximate those generally used in horticultural practice.

Color references are made to The Royal Horticultural Society (R.H.S.) Colour Chart, except where general color terms of ordinary significance are used. The color references are approximate, as color depends to a degree on horticultural practices such as light level and degree of fertilization, among others. The color values were determined between 11:00 a.m. and 3:00 p.m. on Mar. 25, 2003, under 5000 lux natural light in a glasshouse in Bleiswijk, The Netherlands. The phenotype may vary significantly when grown under different conditions of temperature, light or other determining factors, without a change in genotype of the plant.

Propagation: Asexual propagation by means of tissue culture and all subsequent propagation that flowered have been true to the original type in plant and flower characteristics.

Plant description: Approximately 55–60 weeks following division, 'Anthbnena' will reach a mature size of approximately 30 cm to 35 cm in height and approximately 30 cm to 35 cm in width in a 14 cm pot. However, 'Anthbnena' can be easily grown to a larger size plant, for example 40 cm in height, when it is placed in a 17 cm pot.

Leaves:

*Form.*—The leaf blade is elliptical-cordate with an acuminate tip and a cordate base. The leaf blade angle with the petiole between 110 and 150 degrees. 'Anthbnena' makes larger leaf blades as it ages. 'Anthbnena' also produces a lot of axillary shoots with smaller leaf blades. Therefore, a wide range in leaf blade length and width is found on each plant. The minimum leaf blade length is approximately 4 cm and the maximum leaf blade length is approximately 17 cm. The minimum leaf blade width is approximately 2.5 cm and the maximum leaf blade width is approximately 11 cm.

*Texture.*—The leaf blades are shiny, leatherly and thick. The mature leaf blades are weakly cupped. The young leaf blades have more shine than the old leaf blades.

*Veins.*—The mid-vein and primary veins (the veins which radiate out from the juncture of the petiole and leaf) protrude at the underside of the leaf blade. These veins are green (RHS 137C) in the upper surface and the lower surface (RHS 146D) and contrast with the green color of the surface of the leaf blade.

*Leaf blade-color.*—Young leaf blade (approximately maximum 4 weeks old) upper surface is green (RHS 146A). Mature leaf blade (approximately more than 4 weeks) upper surface is green (RHS 139A) and the lower surface is light green (RHS 137B).

*Lobes.*—A leaf blade has two small lobes extending past the petiole. The distance between the petiole and leaf juncture to the highest point on the lobes of mature leaf blades (width 10 cm, length 17 cm) ranges approximately from 3.5 to 4.5 cm.

*Petiole.*—The color of the petiole of a mature leaf blade is green (RHS 137B). The color of the petiole of a young leaf blade is brown-orange (RHS 164A). The cross section petiole is round and the diameter is approximately 2 to 3 mm. The color of the cataphyls surrounding the petioles is light-green (RHS 144B) with a bit reddish tip (179A).

Spathe:

*Buds.*—The spathe is tightly rolled around the spadix and extrudes from the peduncle sheath. After the spathe is fully open the peduncle elongates some extra centimeters.

*Size.*—The completely developed spathe of a 35 cm tall plant is approximately 7 cm long and approximately 9 cm width.

*Color.*—When the spathe has just fully opened, the upper surface is red (RHS 53B) and the lower surface is red (RHS 53C). Approximately 7 to 8 weeks after the opening of the spathe discolors to brown-red (RHS 185A). The red color slightly disappears. After approximately another 14 to 16 weeks the complete flower will die off. The edge of the lobes of the spathe is light green (RHS 144A) on the upper surface and green (RHS 146D) on the lower surface. It depends on cultural circumstances, like time of year whether the edges of the lobes will be green or not.

*Arrangement.*—The spathe angle with the peduncle is between 80 and 100 degrees. The spathe stands on a slightly curved wiry peduncle approximately 5 cm to 10 cm above the foliage. The peduncle cross-section is round and the diameter approximately 3 mm to 4 mm, depending on the age of the plant. The peduncle is erect and its length on the plant depends on the age of the plant. It ranges from approximately 20 to 25 cm.

*Shape.*—The spathe is ovate with a mucronate tip and a cordate base. A fully opened spathe is cupped. The lobes of the flowers stay open and are free. When the flower ages the lobes could bend outward.

Flowering time: One small untreated tissue culture plant of approximately 2 cm tall will flower, depending on season, after approximately 15 to 16 months when approximately 2 to 3 blossoms will appear. More blossoms appear after some extra weeks so that a full flowering and salable plant can have 4 to 10 red flowers. Smaller blossoms may occur on less mature growth.

Reproductive organs:

*Size.*—The spadix measures approximately 2.5 to 4 cm in height. The length of the spadix is shorter than the length of the spathe. The spadix is a little columnar. The width of a mature spadix that is approximately 4 cm long is approximately 6 mm to 8 mm at the base and approximately 5 mm to 7 mm at the top. The spadix angle with spathe is approximately 80 to 100 degrees.

*Color.*—At the time the spathe unrolls the spadix is fully unripe. Later the spadix will mature; pistils become visible and pollen occurs. An unripe spadix is green-yellow (RHS 153D) and a ripe spadix is greyed-white (RHS 156D). As the spadix matures (from base to tip) it becomes fully white. When the flower ages the spadix becomes green (RHS 141A) with white pistils.

*Stamens.*—Anthers and filaments are not clearly visible on the spadix.

*Pollen.*—Minimal pollen production; white in color.

*Pistil.*—An unripe pistil is green-yellow (RHS 153D) and a ripe pistil is white (RHS 54B). The pistil protrudes from the spadix.

Roots: Light pink to light brown roots with smaller hairy laterals. The root-tips are yellow.

Disease/pest resistance: No known resistance and/or susceptibility to diseases and pests.

I claim:

1. A new and distinct *Anthurium andreanum* plant named 'Anthbnena', as herein described and illustrated.

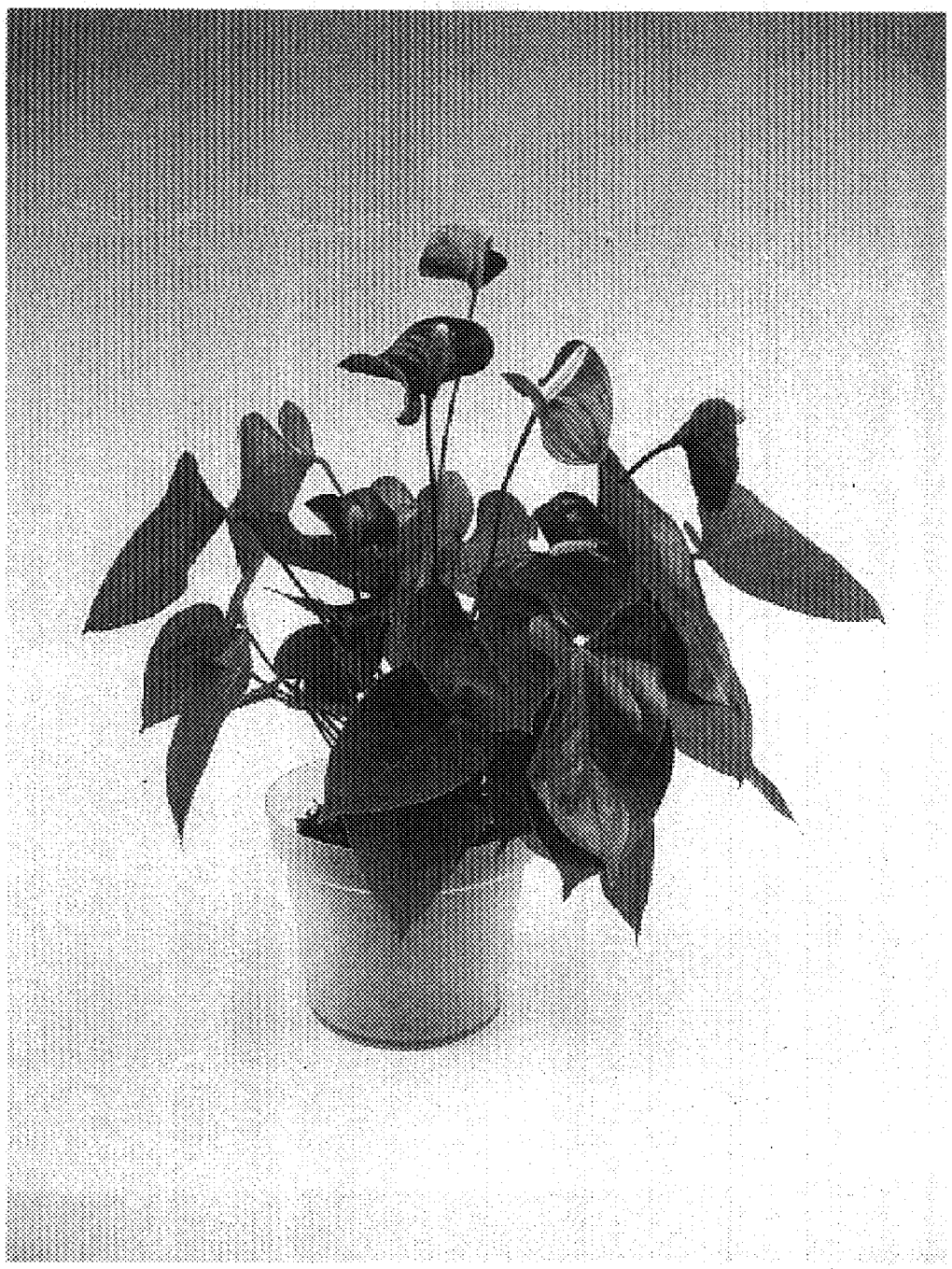

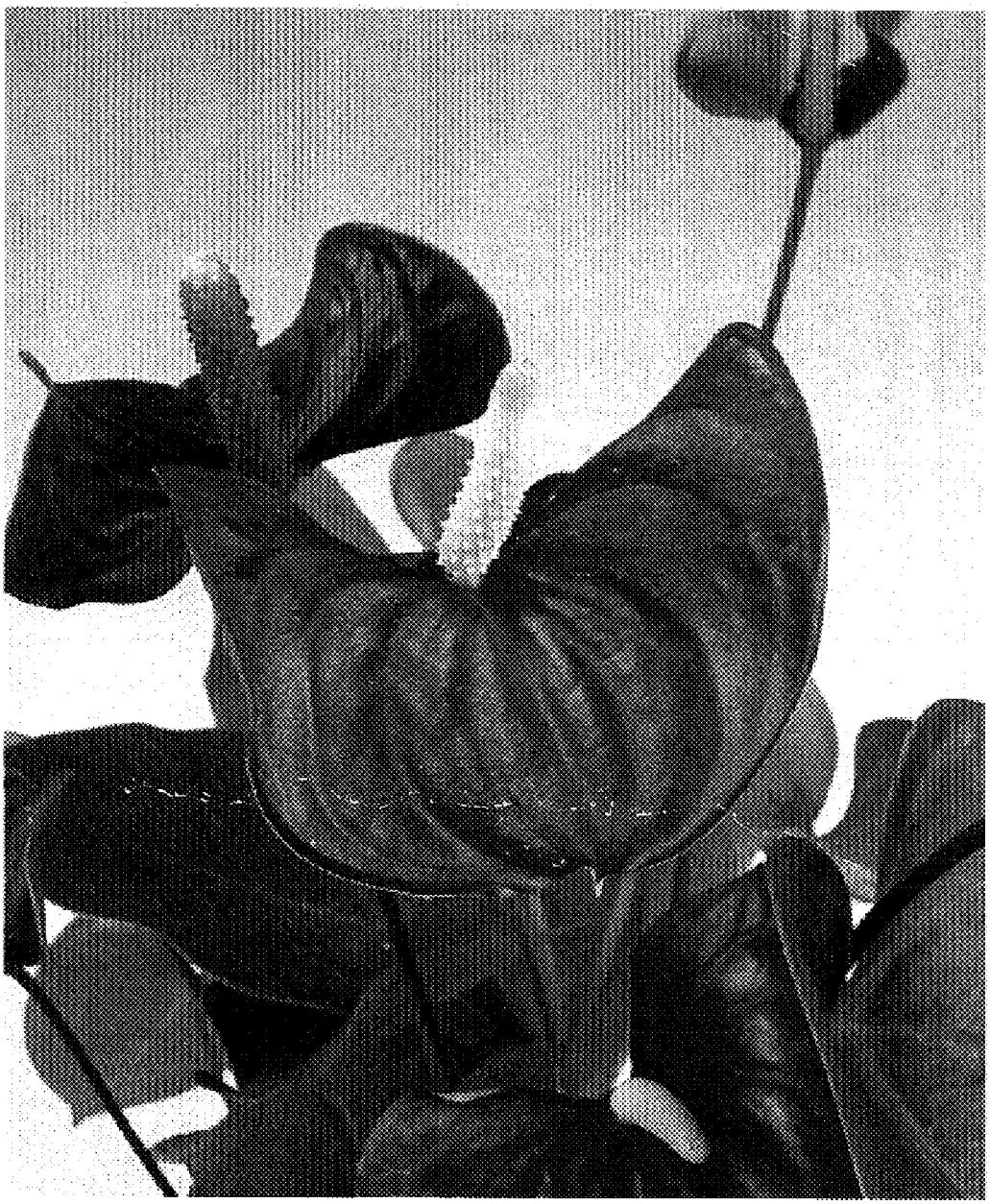

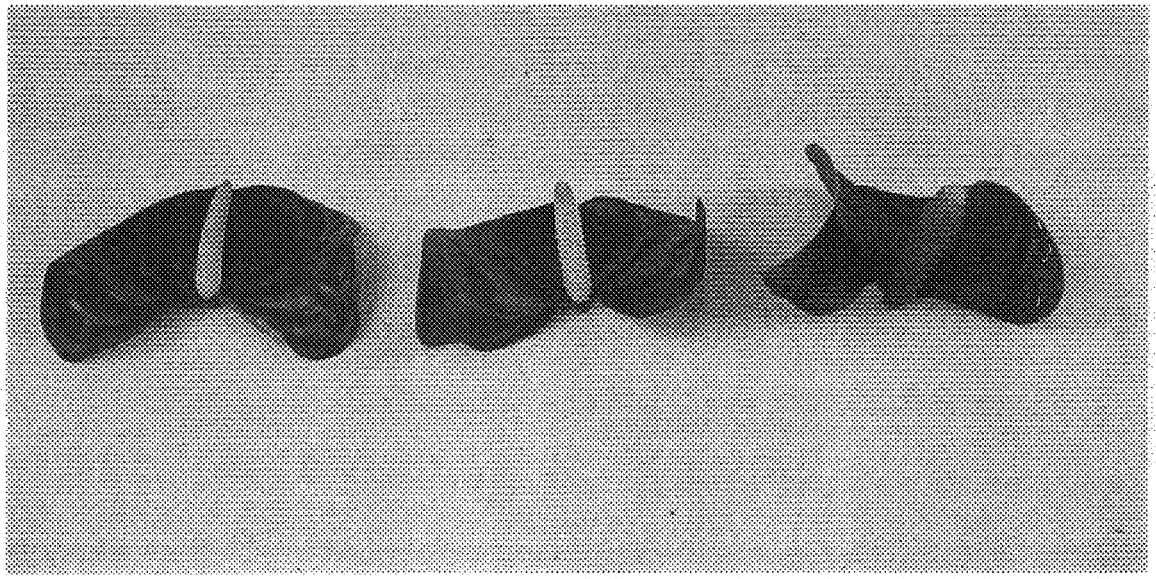

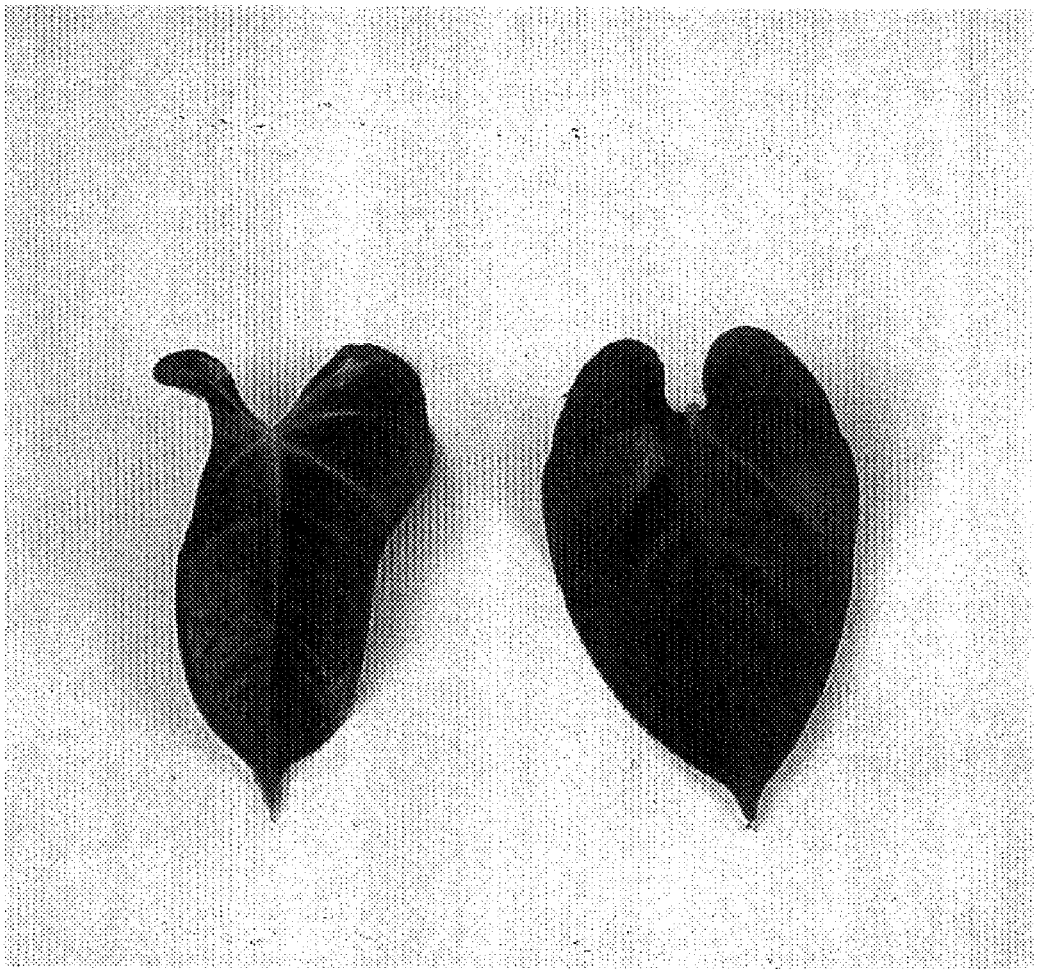

* * * * *